(12) United States Patent
Hofmeister et al.

(10) Patent No.: US 6,399,824 B1
(45) Date of Patent: Jun. 4, 2002

(54) SUBSTITUTED CINNAMIC, ACID GUANIDIDES, PROCESS FOR THEIR PREPARATION, THEIR USE AS A MEDICAMENT, AND MEDICAMENT COMPRISING THEM

(75) Inventors: Armin Hofmeister, Nierstein; Max Hropot, Flörsheim; Uwe Heinelt, Wiesbaden; Markus Bleich, Hünfelden-Dauborn; Hans-Jochen Lang, Hofheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/954,016

(22) Filed: Sep. 18, 2001

(30) Foreign Application Priority Data

Sep. 22, 2000 (DE) .......................... 100 46 993

(51) Int. Cl.$^7$ .......................... C07I 311/16; A61K 31/18
(52) U.S. Cl. .......................... 564/86; 514/255; 514/426; 514/428; 514/592; 514/593; 514/603; 544/383; 548/557; 548/567; 548/568; 548/569; 564/40; 564/41; 564/42
(58) Field of Search .............................. 564/86, 40.41, 564/42, 133.134; 544/383; 548/557, 567, 568, 569; 514/255, 428, 426, 592, 593, 603, 824, 921

(56) References Cited

U.S. PATENT DOCUMENTS

| 5,883,133 A | 3/1999 | Schwark et al. |
| 6,005,010 A | 12/1999 | Schwark et al. |
| 6,057,322 A | 5/2000 | Kleemann et al. |
| 2001/0020042 A1 | 9/2001 | Schwark et al. |

FOREIGN PATENT DOCUMENTS

| DE | 195 02 795 | 8/1996 |
| EP | 0 723 956 | 7/1996 |
| EP | 0 744 397 | 11/1996 |
| EP | 0 825 178 | 2/1998 |
| EP | 0 755 919 B1 | 11/1999 |

OTHER PUBLICATIONS

Derwent Abstract of EP 0 755 919, 1997.
Derwent Abstract of DE 195 02 795, 1996.
Derwent Abstract of EP 0 723 956, 1996.
Derwent Abstract of EP 0 825 178, 1998.
Derwent Abstract of EP 0 744 397, 1996.
PCT International Search report of Jan. 9, 2002.

*Primary Examiner*—Shailendra Kumar
(74) *Attorney, Agent, or Firm*—Finnegan, Henderson, Farabow, Garrett & Dunner, LLP

(57) ABSTRACT

Substituted cinnamic acid guanidides, process for their preparation, their use as a medicament or diagnostic, and medicament comprising them. Compounds of the formula I

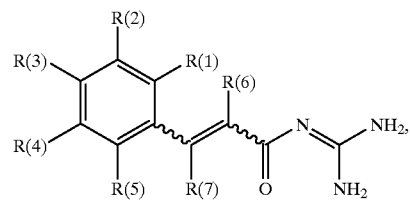

which may be obtained by reaction of a compound II

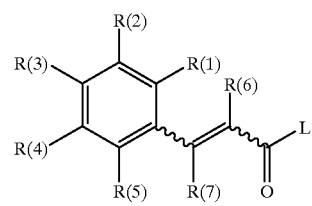

with guanidine.

15 Claims, No Drawings

SUBSTITUTED CINNAMIC, ACID GUANIDIDES, PROCESS FOR THEIR PREPARATION, THEIR USE AS A MEDICAMENT, AND MEDICAMENT COMPRISING THEM

This application claims the benefit of foreign priority under 35 U.S.C. §119 of German patent application no. 10046993.0, filed on Sep. 22, 2000, the contents of which are incorporated by reference herein.

The invention relates to substituted cinnamic acid guanidides of the formula I

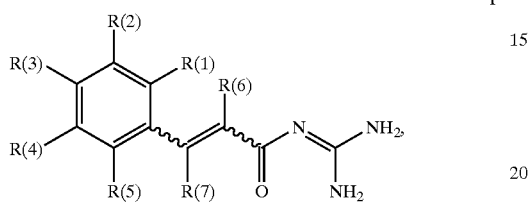

in which:

at least one of R(1), R(2), R(3), R(4) and R(5) is —$X_a$—$Y_b$—$L_n$—U;

X is CR(16)R(17), O, S or NR(18);
  where R(16), R(17) and R(18) independently of one another are H or an alkyl having 1, 2, 3 or 4 carbon atoms, where the alkyl is chosen from unsubstituted alkyls, partially fluorinated alkyls and completely fluorinated alkyls;
a is zero or;
Y is alkylene having 1, 2, 3, 4, 5, 6, 7 or 8 carbon atoms, alkylene-T having 1, 2, 3, 4, 5, 6, 7 or 8 carbon atoms in the alkylene group, T, or T-alkylene having 1, 2, 3, 4, 5, 6, 7 or 8 carbon atoms in the alkylene group;
  where T is NR(20), phenylene, O or S, where the phenylene is not substituted or is substituted by 1–3 substituents chosen from F, Cl, $CF_3$, methyl, methoxy and NR(21)R(22);
    where R(20), R(21) and R(22) independently of one another are H or an alkyl having 1, 2, 3 or 4 carbon atoms, where the alkyl is chosen from unsubstituted alkyls, partially fluorinated alkyls and completely fluorinated alkyls;
b is zero or 1;
L is O, S, NR(23) or $C_kH_{2k}$;
  where k is 1, 2, 3, 4, 5, 6, 7 or 8;
  where R(23) is H or an alkyl group having 1, 2, 3 or 4 carbon atoms, where the alkyl is chosen from unsubstituted alkyls, partially fluorinated alkyls and completely fluorinated alkyls;
n is zero or 1;
U is

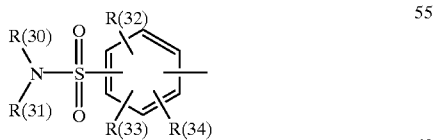

or a nitrogen-containing heterocycle having 1, 2, 3, 4, 5, 6, 7, 8 or 9 carbon atoms, which is substituted by an —$SO_2$NR(30)R(31)-group;
  where R(30) and R(31) independently of one another are H or an alkyl group having 1, 2, 3, 4, 5, 6, 7 or 8 carbon atoms, where in the alkyl group, independently of one another, one or more $CH_2$ groups can be replaced by O, NR(35), C═O, S or C═S;
  where R(35) is H or alkyl having 1, 2, 3 or 4 carbon atoms, where the alkyl is chosen from unsubstituted alkyls, partially fluorinated alkyls and completely fluorinated alkyls; or
R(30) and R(31) independently of one another are H, an alkyl having 1, 2, 3, 4, 5, 6, 7 or 8 carbon atoms, where the alkyl is chosen from partially fluorinated alkyls and completely fluorinated alkyls, ($C_3$–$C_8$)-cycloalkyl, phenyl-($C_1$–$C_4$)-alkyl or ($C_3$–$C_8$)-cycloalkyl-($C_1$–$C_4$)-alkyl,
  where in the alkyl or in the cycloalkyl ring, independently of one another, one or more $CH_2$ groups can be replaced by 0, NR(35), C═O, S or C═S; or
R(30) and R(31) together are 4 or 5 methylene groups,
  where, independently of one another, one or more $CH_2$ groups can be replaced by O, NR(35), C═O, S or C═S; or
R(31) and R(35) together are 4 or 5 methylene groups;
R(32), R(33) and R(34) independently of one another are H, F, Cl, Br, I, ($C_1$–$C_4$)-alkyl, partially fluorinated ($C_1$–$C_4$)-alkyl, completely fluorinated ($C_1$–$C_4$)-alkyl, O—($C_1$–$C_4$)-alkyl, partially fluorinated O—($C_1$–$C_4$)-alkyl, completely fluorinated O—($C_1$–$C_4$)-alkyl, $NO_2$, or NR(28)R(29);
  where R(28) and R(29) independently of one another are H or an alkyl having 1, 2, 3 or 4 carbon atoms, where the alkyl is chosen from unsubstituted alkyls, partially fluorinated alkyls and completely fluorinated alkyls;
  where the N-containing heterocycles are N- or C-bridged and are unsubstituted or are substituted by 1–3 substituents selected from the group consisting of F, Cl, $CF_3$, methyl, methoxy and NR(36)R(37);
R(36) and R(37) independently of one another are H, an alkyl having 1, 2, 3 or 4 carbon atoms, where the alkyl is chosen from unsubstituted alkyls, partially fluorinated, and completely fluorinated alkyls, or benzyl;
and the remaining substituents of R(1), R(2), R(3), R(4) and R(5) independently of one another are H, F, Cl, Br, I, $SO_2NH_2$, $SO_2CH_3$, $NO_2$, NR(24)R(25), CN, unsubstituted ($C_1$–$C_8$)-alkyl, partially fluorinated ($C_1$–$C_8$)-alkyl, completely fluorinated ($C_1$–$C_8$)-alkyl, unsubstituted O—($C_1$–$C_8$)-alkyl, partially fluorinated O—($C_1$–$C_8$)-alkyl, completely fluorinated O—($C_1$–$C_8$)-alkyl, ($C_3$–$C_8$)-cycloalkyl, ($C_3$–$C_8$)-cycloalkyl-($C_1$–$C_4$)-alkyl or phenyl-($C_1$–$C_4$)-alkyl,
  where the phenyl is not substituted or is substituted by 1–3 substituents selected from the group consisting of F, Cl, $CF_3$, methyl, methoxy and NR(11)R(12);
R(11), R(12), R(24) and R(25) independently of one another are H or an alkyl having 1, 2, 3 or 4 carbon atoms, where the alkyl is chosen from unsubstituted alkyls, partially fluorinated alkyls and completely fluorinated alkyls;
R(6) and R(7) independently of one another are H, F, Cl, Br, I, CN, an alkyl having 1, 2, 3, 4, 5, 6, 7 or 8 carbon atoms, where the alkyl is chosen from unsubstituted alkyls, partially fluorinated alkyls, and completely fluorinated alkyls, cycloalkyl having 3, 4, 5, 6, 7 or 8 carbon atoms or phenyl, where the phenyl is not substituted or is substituted by 1–3 substituents selected from the group consisting of F, Cl, CF$_3$, methyl, methoxy and NR(14)R(15);

R(14) and R(15) independently of one another are H or an alkyl having 1, 2, 3 or 4 carbon atoms, where the alkyl is chosen from unsubstituted alkyls, partially fluorinated alkyls and completely fluorinated alkyls;

and their pharmaceutically tolerable salts.

In one embodiment, the compounds of the formula I are those in which:

at least one of the substituents R(1), R(2), R(3), R(4) and R(5) is —X—U;

X is CR(16)R(17), O, S or NR(18);

R(16), R(17) and R(18) independently of one another are H or an alkyl having 1, 2, 3 or 4 carbon atoms, where the alkyl is chosen from unsubstituted alkyls, partially fluorinated alkyls and completely fluorinated alkyls;

U is

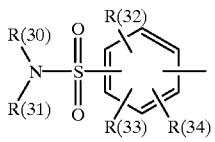

or a nitrogen-containing heterocycle having 1, 2, 3, 4, 5, 6, 7, 8 or 9 carbon atoms, which is substituted by an —SO$_2$NR(30)R(31)-group;

R(30) and R(31) independently of one another are hydrogen or alkyl having 1, 2, 3, 4, 5, 6, 7 or 8 carbon atoms, where in the alkyl chain, independently of one another, one or more CH$_2$ groups can be replaced by O, NR(35), C=O, S or C=S;

R(35) is H or an alkyl having 1, 2, 3, 4 or 5 carbon atoms, where the alkyl is chosen from unsubstituted alkyls, partially fluorinated alkyls and completely fluorinated alkyls; or R(30) and R(31) independently of one another are H, an alkyl having 1, 2, 3, 4, 5, 6, 7 or 8 carbon atoms, where the alkyl is chosen from partially fluorinated alkyl and completely fluorinated alkyl, (C$_3$–C$_8$)-cycloalkyl, phenyl-(C$_1$–C$_4$)-alkyl or (C$_3$–C$_8$)-cycloalkyl-(C$_1$–C$_4$)-alkyl, where in the alkyl or in the cycloalkyl ring, independently of one another, one or more CH$_2$ groups can be replaced by O, NR(35), C=O, S or C=S; or R(30) and R(31) together are 4 or 5 methylene groups, where, independently of one another, one or more CH2 groups can be replaced by O, NR(35), C=O, S or C=S; or R(31) and R(35) together are 4 or 5 methylene groups;

R(32), R(33) and R(34) independently of one another are H, F, Cl, Br, I, (C$_1$–C$_4$)-alkyl, O—(C$_1$–C$_4$)-alkyl, CF$_3$ or NR(28)R(29);

R(28) and R(29) independently of one another are H or alkyl having 1, 2, 3 or 4 carbon atoms;

where the N-containing heterocycles are N- or C-bridged and are not substituted or are substituted by 1–3 substituents selected from the group consisting of F, Cl, CF$_3$, methyl, methoxy and NR(36)R(37);

R(36) and R(37) independently of one another are H, an alkyl having 1, 2, 3 or 4 carbon atoms, where the alkyl is chosen from unsubstituted alkyls, partially fluorinated, and completely fluorinated alkyls, or benzyl;

and the remaining substituents of R(1), R(2), R(3), R(4) and R(5) independently of one another are H, F, Cl, Br, I, SO$_2$NH$_2$, SO$_2$CH$_3$, NO$_2$, NR(24)R(25), CN, unsubstituted (C$_1$–C$_4$)-alkyl, partially fluorinated (C$_1$–C$_4$)-alkyl, completely fluorinated (C$_1$–C$_4$)-alkyl, unsubstituted O—(C$_1$–C$_4$)-alkyl, partially fluorinated O—(C$_1$–C$_4$)-alkyl, completely fluorinated O—(C$_1$–C$_4$)-alkyl, (C$_3$–C$_6$)-cycloalkyl, (C$_3$–C$_6$)-cycloalkyl-(C$_1$–C$_4$)-alkyl or phenyl-(C$_1$–C$_4$)-alkyl, where the phenyl is not substituted or is substituted by 1–3 substituents selected from the group consisting of F, Cl, CF$_3$, methyl, methoxy and NR(11)R(12);

R(11), R(12), R(24) and R(25) independently of one another are H or an alkyl having 1, 2, 3 or 4 carbon atoms, where the alkyl is chosen from unsubstituted alkyls, partially fluorinated alkyls, and completely fluorinated alkyls;

R(6) and R(7) independently of one another are hydrogen, F, Cl, Br, I, CN, an alkyl having 1, 2, 3, 4, 5, 6, 7 or 8 carbon atoms, where the alkyl is chosen from unsubstituted alkyls, partially fluorinated alkyls, and completely fluorinated alkyls, cycloalkyl having 3, 4, 5, 6, 7 or 8 carbon atoms or phenyl, which is not substituted or is substituted by 1–3 substituents selected from the group consisting of F, Cl, CF$_3$, methyl, methoxy and NR(1 4)R(1 5);

R(14) and R(15) independently of one another are H, alkyl having 1, 2, 3 or 4 carbon atoms, where the alkyls are chosen from unsubstituted alkyls, partially fluorinated alkyls and completely fluorinated alkyls;

and their pharmaceutically tolerable salts.

In another embodiment, the compounds of the formula I are those in which:

at least one of the substituents R(1), R(2), R(3), R(4) and R(5) is —X—U;

X is CR(16)R(17), O, S or NR(18);

R(16), R(17) and R(18) independently of one another are H, alkyl having 1, 2, 3 or 4 carbon atoms or CF$_3$;

U is

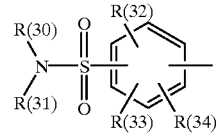

or a nitrogen-containing heterocycle having 1, 2, 3, 4, 5 or 6 carbon atoms, which is substituted by an —SO$_2$NR(30)R(31) group;

R(30) and R(31) independently of one another are H, alkyl having 1, 2, 3, 4, 5, 6, 7 or 8 carbon atoms, CF$_3$, (C$_3$–C$_8$)-cycloalkyl, where in the alkyl, independently of one another, one or more CH$_2$ groups can be replaced by O, NR(35), C=O, S or C=S;

where R(35) is H or alkyl having 1, 2, 3, 4 or 5 carbon atoms; or

R(30) and R(31) together are 4 or 5 methylene groups, where, independently of one another, one or more CH$_2$ groups can be replaced by O, NR(35), C=O, S or C=S; or R(31) and R(35) together are 4 or 5 methylene groups;

R(32), R(33) and R(34) independently of one another are H, F, Cl, methyl, ethyl, Omethyl, Oethyl, $CF_3$, $NH_2$, NHmethyl or Nmethyl$_2$;

where the N-containing heterocycles are N- or C-bridged and are not substituted or are substituted by 1–3 substituents selected from the group consisting of F, Cl, $CF_3$, methyl, methoxy and NR(36)R(37);

R(36) and R(37) independently of one another are H, alkyl having 1, 2, 3 or 4 carbon atoms, $CF_3$ or benzyl;

and the remaining substituents of R(1), R(2), R(3), R(4) and R(5) independently of one another are H, F, Cl, Br, I, $SO_2NH_2$, $SO_2CH_3$, NR(24)R(25), CN, ($C_1$–$C_4$)-alkyl, $CF_3$, $C_2F_5$, O—($C_1$–$C_4$)-alkyl, $OCF_3$, $OC_2F_5$, ($C_3$–$C_6$)-cycloalkyl, ($C_3$–$C_6$)-cycloalkyl-($C_1$–$C_4$)-alkyl or phenyl-($C_1$–$C_4$)-alkyl, where the phenyl is not substituted or is substituted by 1–3 substituents selected from the group consisting of F, Cl, $CF_3$, methyl, methoxy and NR(11)R(12);

R(11), R(12), R(24) and R(25) independently of one another are H or alkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, $CF_3$, cycloalkyl having 3, 4, 5 or 6 carbon atoms;

and their pharmaceutically tolerable salts.

In a further embodiment, compounds of the formula I are those in which:

at least one of the substituents R(1), R(2), R(3), R(4) and R(5) is —X—U;

X is CR(16)R(17), O, S or NR(18);

R(16), R(17) and R(18) independently of one another are H, $CH_3$, $C_2H_5$ or $CF_3$;

U is

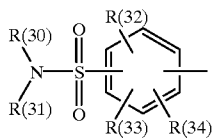

or an N-containing heterocycle having 3, 4 or 5 carbon atoms, which is substituted by an —$SO_2$NR(30)R(31)-group;

R(30) and R(31) independently of one another are hydrogen or alkyl having 1, 2, 3, 4, 5, 6, 7 or 8 carbon atoms, $CF_3$, ($C_3$–$C_8$)-cycloalkyl;

where in the alkyl, independently of one another, one or more $CH_2$ groups can be replaced by O, NR(35), C=O, S or C=S;

R(35) is H or alkyl having 1, 2, 3, 4 or 5 carbon atoms; or

R(30) and R(31) together are 4 or 5 methylene groups, where, independently of one another, one or more $CH_2$ groups can be replaced by O, NR(35), C=O, S or C=S; or R(31) and R(35) together are 4 or 5 methylene groups;

R(32), R(33) and R(34) independently of one another are H, F, Cl, methyl, $CF_3$;

where the N-containing heterocycles are N- or C-bridged and are not substituted or are substituted by 1–3 substituents selected from the group consisting of F, Cl, $CF_3$, methyl, methoxy and NR(36)R(37);

R(36) and R(37) independently of one another are H, $CH_3$, $C_2H_5$ or $CF_3$;

and the remaining substituents of R(1), R(2), R(3), R(4) and R(5) independently of one another are H, F, Cl, $SO_2NH_2$, $SO_2CH_3$, NR(24)R(25), CN, ($C_1$–$C_4$)-alkyl, $CF_3$, $C_2F_5$, O—($C_1$–$C_4$)-alkyl, $OCF_3$, $OC_2F_5$, ($C_3$–$C_6$)-cycloalkyl or ($C_3$–$C_6$)-cycloalkyl-($C_1$–$C_4$)-alkyl;

R(24) and R(25) independently of one another are H, alkyl having 1, 2, 3 or 4 carbon atoms;

R(6) and R(7) independently of one another are H, F, Cl, Br, I, CN, $CH_3$, $C_2H_5$, $CF_3$ or cycloalkyl having 3, 4, 5 or 6 carbon atoms;

and their pharmaceutically tolerable salts.

If the compounds of the formula I contain one or more centers of asymmetry, these can have either the S or R configuration. The compounds may be present as optical isomers, as diastereomers, as racemates or as mixtures thereof, including mixtures of at least one stereoisomeric form and at least one pharmaceutically tolerable salt.

The double bond geometry of the compounds of the formula I may be either E or Z. The compounds may be present in a mixture of double bond isomers.

The designated alkyls, including substituted alkyls partially fluorinated alkyls and completely fluorinated alkyls may be chosen from straight-chain alkyls or branched alkyls.

N-containing heterocycles having 1, 2, 3, 4, 5, 6, 7, 8 or 9 carbon atoms include, but at not limited to, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, isoindolyl, benzimidazolyl, indazolyl, quinolyl, isoquinolyl, phthalazinyl, quinoxalinyl, quinazolinyl, cinnolinyl.

In one embodiment, the N-containing heterocycles are chosen from pyrrolyl, imidazolyl, pyrazolyl, pyridyl, pyrazinyl, pyrimidinyl and pyridazinyl.

In a further embodiment, the N-containing heterocycles is chosen from Pyridyl.

The invention furthermore relates to a process for the preparation of the compounds I, which comprises reacting a compound of the formula II

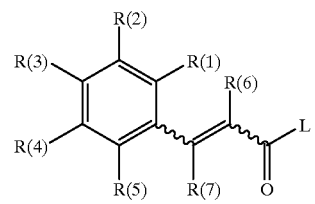

II in which R(1) to R(7) have the meanings indicated and L is an easily nucleophilically substitutable leaving group, with guanidine.

Examples of leaving groups include, but are not limited to,: —OMe, —OEt, —OPh, —SPh, —SMe, and 1-imidazolyl.

The activated acid derivatives of the formula 11, in which L is an alkoxy group, for example a methoxy group, a phenoxy group, phenylthio group, methylthio group or 2-pyridylthio group, a nitrogen heterocycle, for example 1-imidazolyl, may be obtained, for example, in a manner known per se from the carboxylic acid chlorides on which they are based (formula II, L=Cl), which for their part may in turn be prepared in a manner known per se from the carboxylic acids on which they are based (formula II, L=OH), for example using thionyl chloride.

Beside the carboxylic acid chlorides of the formula II (L=Cl), other activated acid derivatives of the formula II may also be prepared directly from the benzoic acid derivatives on which they are based (formula II, L=OH) in a manner known per se, such as the methyl esters of the formula II with L=OCH$_3$ by treating with gaseous HCl in methanol, the imidazolides of the formula II by treating with carbonyldiimidazole [L=1-imidazolyl, Staab, Angew. Chem. Int. Ed. Engl. 1, 351–367 (1962)], the mixed anhydrides II with Cl—COOC$_2$H$_5$ or tosyl chloride in the presence of triethylamine in an inert solvent, and the activation of benzoic acids with dicyclohexylcarbodiimide (DCC) or with O-[(cyano(ethoxycarbonyl)methylene)-amino]-1,1,3,3-tetramethyluroniumtetrafluoroborate ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are given with details of the source literature in J. March, Advanced Organic Chemistry, Third Edition (John Wiley & Sons, 1985), p. 350.

The reaction of an activated carboxylic acid derivative of the formula II with guanidine may be carried out in a manner known per se in a protic or aprotic polar but inert organic solvent. In the reaction with guanidine of the methyl or ethyl benzoates (II, L=Ome, OEt), methanol, isopropanol, DMF or THF from 20° C. up to the boiling temperature of these solvents may be suitable. Most reactions of compounds II with salt-free guanidine may be carried out in aprotic inert solvents such as THF, DMF, dimethoxyethane or dioxane. IN one embodiment, when using a base such as, for example, NaOH, water may also be used as solvent in the reaction of II with guanidine.

When L=Cl, the reaction may be carried out, for example, with addition of an acid scavenger, e.g. in the form of excess guanidine, for the binding of the hydrohalic acid.

Some of the underlying benzoic acid derivatives of the formula II are known and described in the literature. The unknown compounds of the formula II may be prepared by methods known from the literature. The alkenylcarboxylic acids obtained may be reacted by one of the process variants described above to give compounds I according to the invention.

The introduction of some substituents may be achieved by methods known from the literature of palladium-mediated cross-coupling of aryl halides or aryl triflates with, for example, organostannanes, organoboronic acids or organoboranes or organocopper or -zinc compounds.

In general, carboxylguanidines I are weak bases and may bind acid with formation of salts. Possible acid addition salts include, but are not limited to, salts of all pharmacologically tolerable acids, for example halides, such as hydrochlorides, lactates, sulfates, citrates, tartrates, acetates, phosphates, methylsulfonates and p-toluenesulfonates.

The compounds I may be substituted acylguanidines.

Similar cinnamic acid guanidides are disclosed in European laid-open publication 755 919 (HOE 94/F 168), but these known compounds do not meet all desired requirements. Using the compounds of the formula I, it was possible to achieve improved water solubility, which may result in increased excretion via the kidneys. Moreover, in one embodiment, the compounds of the formula I show a very good inhibitory action on NHE$_3$ (Na$^+$/H$^+$ exchanger subtype 3). This may be achieved by the compounds according to the invention, which, in one embodiment, have no undesired and disadvantageous salidiuretic properties, but very good antiarrhythmic properties, such as are useful, for example, for the treatment of illnesses which are caused by oxygen deficiency. As a result of their pharmacological properties, the compounds may be suitable, as antiarrhythmic pharmaceuticals having a cardioprotective component, for infarct prophylaxis and infarct treatment and also for the treatment of angina pectoris, where they also preventively inhibit or greatly decrease the pathophysiological processes in the formation of ischemically induced damage, in particular in the induction of ischemically induced cardiac arrhythmias.

In one embodiment, because of their protective actions against pathological hypoxic and ischemic situations, the compounds of the formula I according to the invention may be used, as a result of inhibition of the cellular Na$^+$/H$^+$ exchange mechanism, as pharmaceuticals for the treatment of all acute or chronic damage induced by ischemia or illnesses primarily or secondarily induced thereby. This relates to their use as pharmaceuticals for surgical interventions, e.g. in organ transplantation, where the compounds may be used both for the protection of the organs in the donor before and during removal, for the protection of removed organs, for example during treatment with or storage thereof in physiological bath fluids, and during transfer to the recipient's body. The compounds may also be valuable pharmaceuticals which have a protective action when carrying out angioplastic surgical interventions, for example on the heart and on peripheral vessels. Corresponding to their protective action against ischemically induced damage, the compounds may also be suitable as pharmaceuticals for the treatment of ischemias of the nervous system, in particular of the CNS, where they may be suitable, for example, for the treatment of stroke or of cerebral edema. Moreover, the compounds of the formula I according to the invention may likewise be suitable for the treatment of forms of shock, such as, for example, of allergic, cardiogenic, hypovolemic and of bacterial shock.

In another embodiment, the compounds may furthermore induce an improvement in the respiratory drive and may therefore be used for the treatment of respiratory conditions in the following clinical conditions and illnesses: impaired central respiratory drive (e.g. central sleep apneas, sudden infant death, postoperative hypoxia), muscle-related respiratory disorders, respiratory disorders after long-term respiration, respiratory disorders during adaptation in a high mountain region, obstructive and mixed forms of sleep apneas, acute and chronic lung diseases with hypoxia and hypercapnia.

The compounds may additionally increase the muscle tone of the upper airways, so that snoring is suppressed.

In one embodiment, a combination of an NHE inhibitor with a carboanhydrase inhibitor (e.g. acetazolamide), the latter producing a metabolic acidosis and thereby even increasing the respiratory activity, proves to be a favorable combination with increased action and decreased use of active compound.

It has been shown that the compounds according to the invention may have a mild laxative effect and accordingly may be used as laxatives or if there is a threat of intestinal blockage, the prevention of the ischemic damage which accompanies blockages in the intestinal area being particularly advantageous.

There is furthermore the possibility of preventing gallstone formation.

In another embodiment, the compounds of the formula I according to the invention may moreover be distinguished by strong inhibitory action of the proliferation of cells, for example, fibroblast cell proliferation and the proliferation of vascular smooth muscle cells. The compounds of the formula I may therefore, in one embodiment, be suitable as valuable therapeutics for illnesses in which cell proliferation is a primary or secondary cause, and may therefore be used as antiatherosclerotics, agents against diabetic late complications, carcinomatous disorders, fibrotic disorders such as pulmonary fibrosis, hepatic fibrosis or renal fibrosis, organ hypertrophies and hyperplasias, in particular in prostate hyperplasia or prostate hypertrophy.

In a further embodiment, the compounds according to the invention may be effective inhibitors of the cellular sodium-proton antiporter ($Na^+/H^+$ exchanger), which is raised in numerous disorders (essential hypertension, atherosclerosis, diabetes etc.) even in those cells which are easily accessible to measurements, such as, for example, in erythrocytes, platelets or leukocytes. The compounds according to the invention may therefore, in one embodiment, be suitable as outstanding and simple scientific tools, for example in their use as diagnostics for the determination and differentiation of certain forms of hypertension, but also of atherosclerosis, of diabetes, proliferative disorders, etc. Moreover, the compounds of the formula I may be suitable for preventive therapy for averting the genesis of high blood pressure, for example of essential hypertension.

It has additionally been found that NHE inhibitors may have a favorable influence on the serum lipoproteins. It is generally recognized that for the formation of arteriosclerotic vascular changes, in particular of coronary heart disease, excessively high blood lipid values, so-called hyperlipoproteinemias, are a significant risk factor. The lowering of raised serum lipoproteins is therefore of extreme importance for the prophylaxis and the regression of atherosclerotic changes. In one embodiment, the compounds according to the invention may therefore be used for the prophylaxis and for the regression of atherosclerotic changes, in that they exclude a causal risk factor. With this protection of the vessels against the endothelial dysfunction syndrome, compounds of the formula I may be valuable pharmaceuticals for the prevention and for the treatment of coronary vasospasms, atherogenesis and atherosclerosis, left-ventricular hypertrophy and dilated cardiomyopathy, and thrombotic disorders.

The compounds mentioned may therefore be used advantageously for the production of a medicament for the prevention and treatment of sleep apneas and muscle-related respiratory disorders; for the production of a medicament for the prevention and treatment of snoring; for the production of a medicament for lowering blood pressure; for the production of a medicament having a laxative effect for the prevention and treatment of intestinal blockages; for the production of a medicament for the prevention and treatment of disorders induced by ischemia and reperfusion of central and peripheral organs, such as acute kidney failure, stroke, endogenous states of shock, intestinal disease etc.; for the production of a medicament for the treatment of hypercholesterolemia; for the production of a medicament for the prevention of atherogenesis and atherosclerosis; for the production of a medicament for the prevention and treatment of diseases which are caused by increased cholesterol levels; for the production of a medicament for the prevention and treatment of diseases which are caused by endothelial dysfunction; for the production of a medicament for the treatment of attack by ectoparasites; for the production of a medicament for the treatment of the illnesses mentioned in combinations with hypotensive substances, preferably with angiotensin-converting enzyme (ACE) inhibitors and angiotensin receptor antagonists. A combination of an NHE inhibitor of the formula I with a blood lipid level-lowering active compound, preferably with an HMG-CoA-reductase inhibitor (e.g. lovastatin or pravastatin), where the latter produces a hypolipidemic action and thereby increases the hypolipidemic properties of the NHE inhibitor of the formula I, proves to be a favorable combination with increased action and decreased use of active compound.

In a further embodiment, the administration of sodium/proton exchange inhibitors of the formula I may be used as novel pharmaceuticals for lowering increased blood lipid levels, and also the combination of sodium/proton exchange inhibitors with hypotensive and/or hypolipidemic pharmaceuticals.

Pharmaceuticals which contain a compound I may in this case be administered, for example, orally, parenterally, intravenously, rectally or by inhalation. In one embodiment, administration is dependent on the particular clinical picture of the disorder. The compounds I may in this case be used on their own or together with pharmaceutical auxiliaries, to be specific both in veterinary and in human medicine.

The person skilled in the art is familiar on the basis of his expert knowledge with auxiliaries which are suitable for the desired pharmaceutical formulation. Beside solvents, gel-forming agents, suppository bases, tablet auxiliaries and other active compound excipients, it is possible to use, for example, antioxidants, dispersants, emulsifiers, antifoams, flavor corrigents, preservatives, solubilizers or colorants.

For an oral administration form, the active compounds may, for example, be mixed with the additives suitable for this, such as excipients, stabilizers or inert diluents, and are brought by means of the customary methods into the suitable administration forms, such as tablets, coated tablets, hard gelatin capsules, or aqueous, alcoholic or oily solutions. Inert excipients which can be used are, for example, gum arabic, magnesia, magnesium carbonate, potassium phosphate, lactose, glucose or starch, in particular corn starch. In this case preparation can take place either as dry or as moist granules. Suitable oily excipients or solvents are, for example, vegetable or animal oils, such as sunflower oil or cod liver oil.

For subcutaneous or intravenous administration, the active compounds may be brought into solution, suspension or emulsion, if desired using the substances customary for this, such as solubilizers, emulsifiers or other auxiliaries. Possible solvents are, for example: water, physiological saline solution or alcohols, e.g. ethanol, propanol, glycerol, in addition also sugar solutions such as glucose or mannitol solutions, or alternatively a mixture of the various solvents mentioned.

Suitable pharmaceutical formulations for administration in the form of aerosols or sprays may be, for example, solutions, suspensions or emulsions of the active compound of the formula I in a pharmaceutically acceptable solvent, such as, in particular, ethanol or water, or a mixture of such solvents.

If desired, the formulation may also contain other pharmaceutical auxiliaries such as surfactants, emulsifiers and stabilizers, as well as a propellant. Such a preparation contains the active compound customarily in a concentration of approximately 0.1 to 10, in particular from approximately 0.3 to 3,% by weight.

The dose of the active compound of the formula I to be administered and the frequency of administrationdepend on the potency and duration of action of the compounds used; additionally also on the nature and severity of the illness to be treated and on the sex, age, weight and individual responsiveness of the mammal to be treated.

On average, the daily dose of a compound of the formula I in the case of a patient approximately 75 kg in weight is at least 0.001 mg/kg, preferably 0.01 mg/kg, to at most 10 mg/kg, preferably 1 mg/kg, of body weight. In acute episodes of the illness, for example, directly after suffering a cardiac infarct, even higher and especially more frequent doses may also be necessary, e.g. up to 4 individual doses per day. In particular on i.v. administration, for example in the case of an infarct patient in. the intensive care unit, up to 200 mg per day may be necessary.

List of abbreviations:

| | |
|---|---|
| MeOH | Methanol |
| DMF | N,N-Dimethylformamide |
| EI | Electron impact |
| DCI | Desorption-chemical ionisation |
| RT | Room temperature |
| EA | Ethyl acetate (EtOAc) |
| mp | Melting point |
| HEP | n-Heptane |
| DME | Dimethoxyethane |
| ES | Electron spray |
| FAB | Fast atom bombardment |
| CI | Chemical ionization |
| $CH_2Cl_2$ | Dichloromethane |
| THF | Tetrahydrofuran |
| eq. | Equivalent |
| TFA | Trifluoroacetate |
| LCMS | Liquid chromatography mass spectroscopy |

EXPERIMENTAL SECTION

General Procedure for the Preparation of Alkenylcarboxylic Acid Guanidides (I)

Variant 1 A: from Alkyl Alkenylcarboxylates (II, L=O-alkyl)

5.0 eq. of potassium tertiary-butoxide are introduced into DMF, treated with 6.0 eq. of guanidine hydrochloride and the mixture is stirred at room temperature for 30 min. 1.0 eq. of the alkyl cinnamate is added to this solution and it is stirred at room temperature until an increase in conversion can no longer be determined by means of a thin-layer chromatogram or CMS. For work-up, the solvent is distilled off under reduced pressure. The residue is taken up in $H_2O$ and treated dropwise with 1N HCl until a precipitate deposits. This is filtered off with suction and washed with EA. The HCl salt of the alkenylcarboxylic acid guanidide thus obtained can be converted into the free cinnamoylguanidine by treatment with bases. In turn, it is possible to prepare other pharmacologically tolerable salts from these by treating with aqueous, methanolic or ethereal solutions of organic or inorganic acids.

Variant 1 B: from Alkenylcarboxylic Acids (II, L=OH)

1.0 eq. of the cinnamic acid derivative is introduced into DMF, 1.1 eq. of carbonyldiimidazole are added and the mixture is stirred at room temperature for 3 h. A solution of the guanidine base, freshly prepared as described under 1 A, is added to this solution and it is additionally stirred at room temperature until complete conversion is achieved, or an increase in conversion can no longer be determined. The work-up is carried out analogously to the procedure described in 1 A.

The retention times ($R_t$) indicated below relate to LCMS measurements using the following parameters:

Stationary phase: Merck Purospher 3p, 2×55 mm
Mobile phase: 95% $H_2O$(0.05% TFA)→95% acetonitrile; 4 min; 95% acetonitrile; 1.5 min→5% acetonitrile; 1 min; 0.5 ml/min.

Example 1

4-[2,6-Difluoro-4-(3-guanidino-2-methyl-3-oxopropenyl) phenoxy]benzenesulfonamide; HCl salt

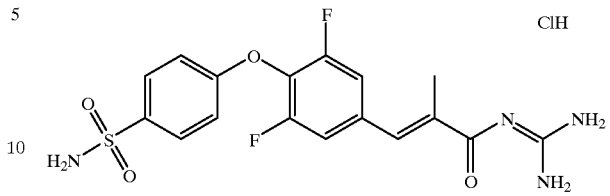

Intermediate 1:
Ethyl 2-methyl-3-(3,4,5-trifluorophenyl)acrylate

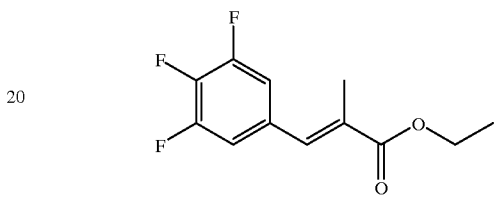

1.0 eq. of 3,4,5-trifluorobenzaldehyde is dissolved in DMF and stirred at room temperature with 1.1 eq. of ethyl 2-(triphenylphosphanylidene)propionate until complete conversion can be determined by means of thin-layer chromatography. The mixture is freed from the solvent and the residue is stirred in diisopropyl ether. The insoluble residue is filtered off, the filtrate is concentrated in vacuo and the residue is chromatographed on silica gel (EA/heptane 1:1), the title compound being obtained in the form of a colorless solid. (M.p.: 66–68° C.).

Intermediate 2:
Ethyl 3-[3,5-difluoro-4-(4-sulfamoylphenoxy)phenyl]-2-methylacrylate

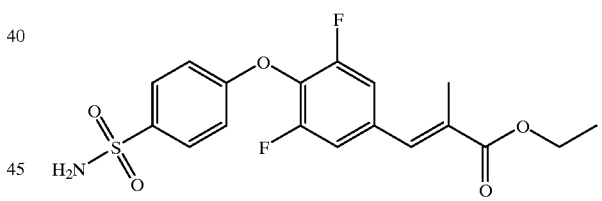

1.5 eq. of 4-hydroxybenzenesulfonamide are treated with the equimolar amount of NaH in dimethylacetamide and deprotonated at room temperature for 1 h. A solution of 1.0 eq. of the intermediate 1 in dimethylacetamide is added dropwise and the reaction mixture is stirred at 150° C. until starting material can no longer be detected by means of TLC or LCMS. For work-up, the solvent is removed in vacuo, the residue is taken up in $H_2O$ and the mixture is extracted 2× with EA. The organic phases are dried using $MgSO_4$ and concentrated. Chromatography on silica gel gives the desired bisphenyl ether as a colorless solid in 40 to 50% of the theoretical yield. (MS-ES+: 398.2; M.p.: 113–115° C.).

4-[2,6-Difluoro-4-(3-guanidino-2-methyl-3-oxopropenyl) phenoxy]benzenesulfonamide; HCl salt The reaction of the intermediate 2 according to the method described under 1 A yields the title compound as a colorless solid. (MS-ES+: 411.0; LCMS-$R_t$=3.710 min).

Example 2

4-[2,6-Difluoro-4-(3-guanidino-2-methyl-3-oxopropenyl) phenoxy]benzenesulfonamide; methanesulfonate

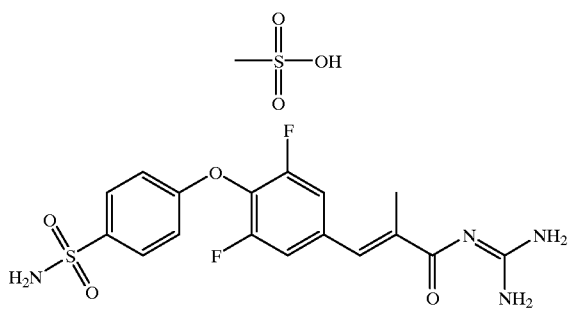

The compound described in Example 1 is converted into the corresponding methanesulfonate using acetonitrile/$H_2O$ mixtures, 1% strength in methanesulfonic acid. (MS-ES+: 411.2; LCMS-$R_t$=3.995 min).

Example 3
4-[4-(3-Guanidino-2-methyl-3-oxopropenyl)phenoxy]benzenesulfonamide; HCl salt

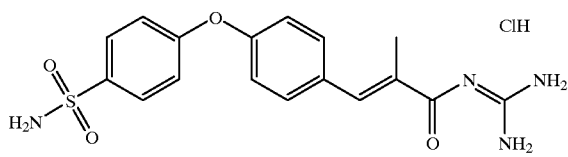

Intermediate 1:
Ethyl 2-methyl-3-(4-fluorophenyl)acrylate

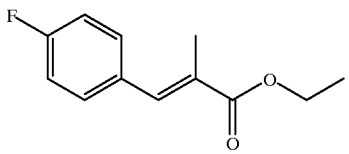

Analogous procedure to that in the case of intermediate 1, starting from 4-fluorobenzaldehyde Example 1 gives the desired cinnamic acid ester in almost quantitative yield as a colorless oil. (MS-CI+: 209.2).

Intermediate 2:
Ethyl 2-methyl-3-[4-(4-sulfamoylphenoxy)phenyl]acrylate

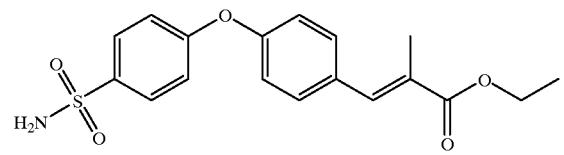

can be prepared according to the procedure described in intermediate 2, Example 1, where on account of the lower reactivity of the monofluoro compound (intermediate 1), lower yields have to be expected. The title compound can be isolated as a colorless oil.
4-[4-(3-Guanidino-2-methyl-3-oxopropenyl)phenoxy]benzenesulfonamide; HCl salt Intermediate 2 is reacted according to the manner described in 1 A, 75% of the desired cinnamic acid guanidide being obtained as a crystalline solid. (MS-ES+: 375.2; LCMS-$R_t$=3.933 min).

Example 4
4-[4-(3-Guanidino-2-methyl-3-oxopropenyl)phenylamino]benzenesulfonamide; trifluoroacetate

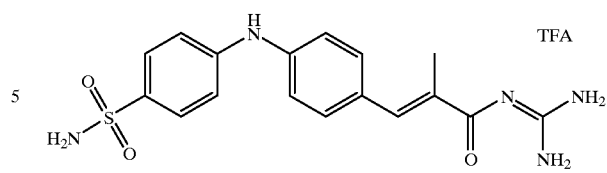

Intermediate 1:
Ethyl 2-methyl-3-(4-bromophenyl)acrylate

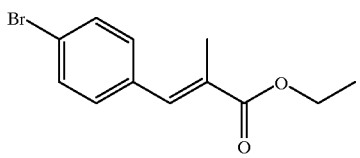

Analogous procedure to that in the case of intermediate 1, starting from 4-bromobenzaldehyde, Example 1 yields the desired cinnamic acid ester in almost quantitative yield as a colorless oil. (MS-CI+: 269.1 /271.1).

Intermediate 2
4-Amino-N-dimethylaminomethylenebenzenesulfonamide

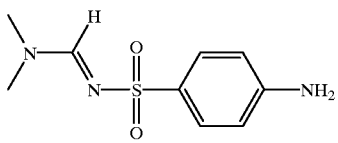

is synthesized in a manner known to the person skilled in the art, starting from 4-aminobenzenesulfonamide and DMF dimethyl acetal (see, for example: J. Med. Chem., 1983, 26, 1174–1187). (MS-ES+: 228.0).

Intermediate 3:
Ethyl 3-{4-[4-(dimethylaminomethylenesulfamoyl)phenylamino]phenyl}-2-methylacrylate

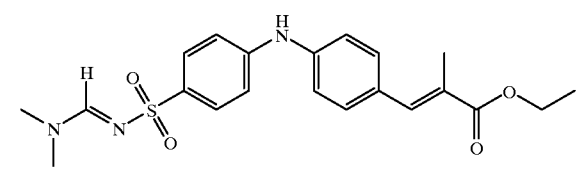

1.4 eq. of $Cs_2CO_3$, 0.03 eq. or $Pd(OAc)_2$, as well as 0.045 eq. of 2,2-bis(diphenyl-phosphino)-1,1'-binaphthalene are introduced in anhydrous toluene under argon. 1.0 eq. of intermediate 1, as well as 1.2 eq. of intermediates 2, are added to this solution and it is stirred at 100° C. under a protective gas atmosphere until complete conversion can be determined (TLC or LCMS). For work-up, it is treated with ether and the resulting precipitate is filtered off. The filtrate is concentrated and purified on silica gel, it being possible to isolate the desired product as a colorless oil. (MS-ES+: 416.3).

Intermediate 4:
2-Methyl-3-[4-(4-sulfamoylphenylamino)phenyl]acrylic acid

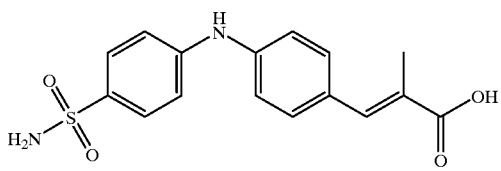

The intermediate 3 is heated at 40 to 60° C. for 4 to 5 h in 2 N NaOH. The mixture is then concentrated in vacuo, the residue is taken up in H₂O and a pH of 6 to 7 is set using 2N HCl, the product depositing in the form of a slightly yellow solid. Filtering off with suction and drying over $P_2O_5$ gives the desired cinnamic acid derivative in a yield of 90%. (MS-ES+: 333.2).

4-[4-(3-Guanidino-2-methyl-3-oxopropenyl)phenylamino]benzenesulfonamide; trifluoroacetate Starting from intermediate 4, the title compound is prepared by the procedure described in 1 B. After HPLC, the product is isolated as a yellowish crystalline solid in a yield of 40 to 50%. (MS-ES+: 374.2; LCMS $R_t$=3.761 min).

Example 5

3-[4-(3-Guanidino-2-methyl-3-oxopropenyl)phenylamino]benzenesulfonamide, trifluoroacetate

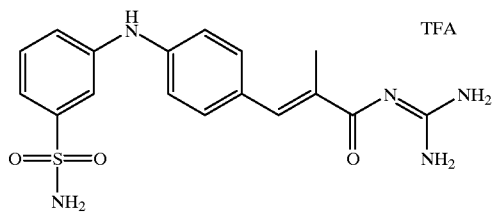

Intermediate 1:

3-Ethyl 2-methyl-3-(4-bromophenyl)acrylate

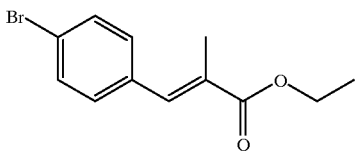

see Example 4

Intermediate 2:

3-Amino-N-dimethylaminomethylenebenzenesulfonamide

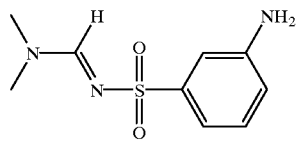

is synthesized in the manner known to the person skilled in the art, starting from 3-aminobenzenesulfonamide and DMF dimethyl acetal (see, for example: J. Med. Chem., 1983, 26, 1174–1187). (MS-ES+: 228.0).

Intermediate 3:

Ethyl 3-{4-[3-(dimethylaminomethylenesulfamoyl)phenylamino]phenyl}-2-methylacrylate

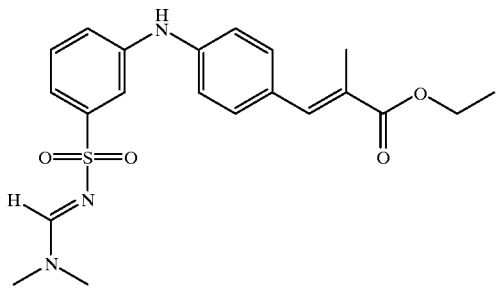

The synthesis of the title compound is carried out to a procedure analogous to intermediate 3, Example 4, it being possible to isolate 77% of the desired product. (MS-ES+: 416.3).

Intermediate 4:

2-Methyl-3-[4-(3-sulfamoylphenylamino)phenyl]acrylic acid

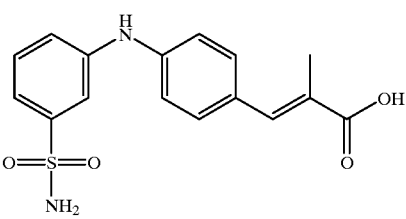

The protective group removal and ester cleavage of intermediate 3 is carried out according to the procedure specified in Example 4, intermediate 4, it being possible to isolate intermediate 4 in the form of a colorless solid in 87% yield. (MS-ES+: 333.1).

3-[4-(3-Guanidino-2-methyl-3-oxopropenyl)phenylamino]benzenesulfonamide, trifluoroacetate Starting from intermediate 4, the title compound is prepared by the procedure described in 1 B. After HPLC, the product is isolated as a yellowish crystalline solid in a yield of 40 to 50%. (MS-ES+: 374.2; LCMS $R_t$=3.851 min).

Example 6

4-[2,6-Difluoro-4-(3-guanidino-2-methyl-3-oxopropenyl)phenoxy]-N-(2-dimethylaminoethyl)benzenesulfonamide, HCl salt

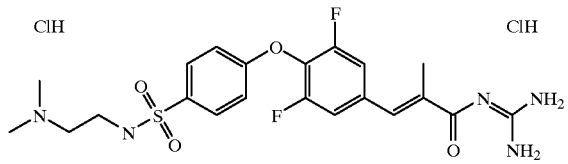

Intermediate 1:
4-Hydroxybenzenesulfonyl chloride

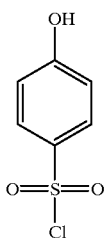

is synthesized by processes known from the literature (R. W. Campbell, H. W. Hill, jr.; J. Org. Chem., 38, 1973, 1047.)
Intermediate 2:
N-(2-Dimethylaminoethyl)-4-hydroxybenzenesulfonamide

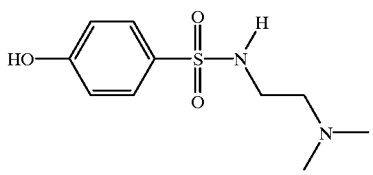

1.0 eq. of the intermediate 1 is introduced in dichloromethane and 2.2 eq. of N,N-dimethylaminoethanediamine, dissolved in dichloromethane, are added dropwise at room temperature and the mixture is stirred at room temperature. After complete conversion has been detected, the mixture is freed from the solvent and the residue is taken up in $H_2O$. It is extracted 2× with EA and the aqueous phase is concentrated in vacuo. The residue is washed once with acetone and recrystallized from hot isopropanol, the sulfonamide being isolated as a colorless solid. (M.P.: 165–168° C.).
Intermediate 3:
Ethyl 2-methyl-3-(3,4,5-trifluorophenyl)acrylate

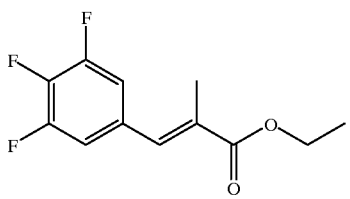

see Example 1.
Intermediate 4:
Ethyl 3-[4-[4-(2-dimethylaminoethylsulfamoyl)phenoxy]-3,5-difluorophenyl}-2methylacrylate

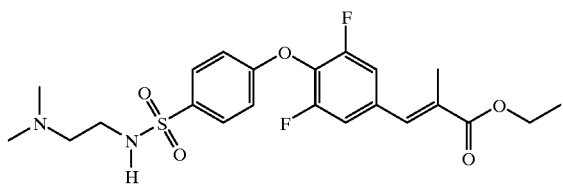

1.5 eq. of intermediate 2 are treated with 1.75 eq. of NaH in dimethylacetamide and the mixture is stirred at 75° C. for 30 min with exclusion of moisture. A solution of 1.0 eq. of intermediate 3 in dimethylacetamide is added thereto and the mixture is stirred at 150° C. until an increase in conversion can no longer be detected (DC, LCMS). For work-up, the mixture is freed from the solvent and the residue is taken in $H_2O$. The aqueous phase is extracted 2× with EA, dried using $MgSO_4$ and concentrated. The crude product thus obtained is purified by chromatography on silica gel.
4-[2,6-Difluoro-4-(3-guanidino-2-methyl-3-oxopropenyl)phenoxy]-N-(2-dimethyl-aminoethyl)benzenesulfonamide, HCl salt Intermediate 4 is converted according to the method described in 1 A into the corresponding cinnamic acid guanidide, which can be isolated in the form of a yellowish solid. (MS-ES+: 482.2; LCMS $R_t$=3.750 min).

Example 7

N-(3-{3,5-Difluoro-4-[4-(4-methylpiperazin-1-sulfonyl)phenoxy]phenyl}-2-methyl-acryloyl)guanidine; trifluoroacetate

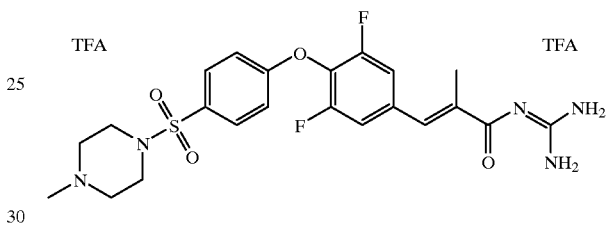

Intermediate 1:
4-Hydroxybenzenesulfonyl chloride

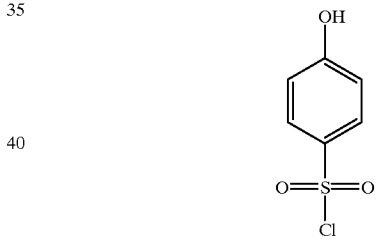

is synthesized according to a process known from the literature (R. W. Campbell, H. W. Hill, jr.; J. Org. Chem., 38, 1973, 1047).
Intermediate 2:
4-(4-Methylpiperazin-1-sulfonyl)phenol

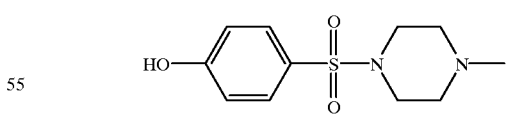

1.0 eq. of intermediate 1 is introduced in dichloromethane and 2.0 eq. of N-methylpiperazine, dissolved in dichloromethane, are added dropwise at room temperature and the mixture is stirred at room temperature. After complete conversion has been determined, the resulting precipitate is filtered off. The filtrate is dried using $MgSO_4$ and freed from the solvent. The crude product thus obtained can be employed in the next step without further purification. (M.p.: 225–227° C.).

Intermediate 3:

Ethyl 2-methyl-3-(3,4,5-trifluorophenyl)acrylate

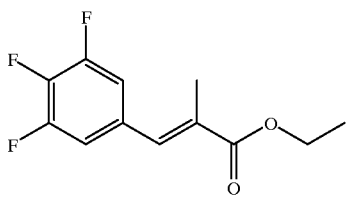

see Example 1.

Intermediate 4:

Ethyl 3-{3,5-difluoro-4-[4-(4-methylpiperazine-1-sulfonyl)phenoxy]phenyl}-2-methylacrylate

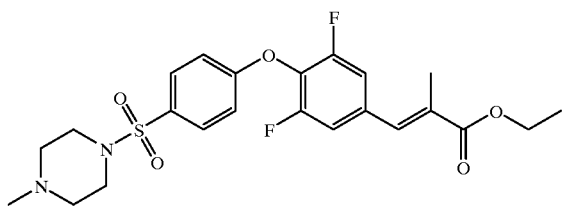

1.0 eq. of intermediate 2 is dissolved in dimethylacetamide and treated with 1.2 eq. of NaH at room temperature. After 30 min at 75° C., a solution of 0.7 eq. of intermediate 3 in dimethylacetamide is added dropwise and the mixture is stirred at 150° C. After conversion is complete, the mixture is freed from the solvent. The residue is taken up in H$_2$O, adjusted to a pH of 7 to 8 and extracted 2× with EA. The organic phases are dried using MgSO$_4$ and concentrated. The residue is purified on silica, the title compound being isolated in a yield of 50 to 60%.

N-(3-{3,5-Difluoro-4-[4-(4-methylpiperazine-1-sulfonyl)phenoxy]phenyl}-2-methylacryloyl)guanidine; trifluoroacetate Intermediate 4 is converted according to the method described in 1 A into the corresponding cinnamic acid guanidide, which can be isolated in the form of a yellowish solid. Final purification by means of HPLC gives the corresponding TFA salt. (MS-ES+: 494.3; LCMS R$_t$=3.809 min).

Example 8

4-[2,6-Difluoro-4-(3-guanidino-2-methyl-3-oxopropenyl)phenoxy]benzenesulfone N-(carboxy-N'-methylamid)amide; HCl salt

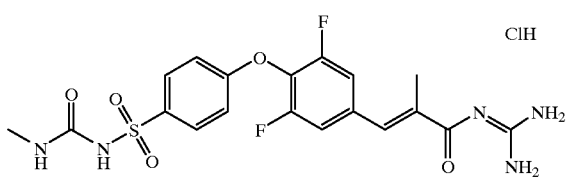

Intermediate 1:

Ethyl 2-methyl-3-(3,4,5-trifluorophenyl)acrylate

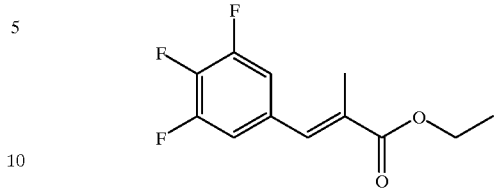

see Example 1.

Intermediate 2:

Ethyl 3-[3,5-difluoro-4-(4-sulfamoylphenoxy)phenyl]-2-methylacrylate

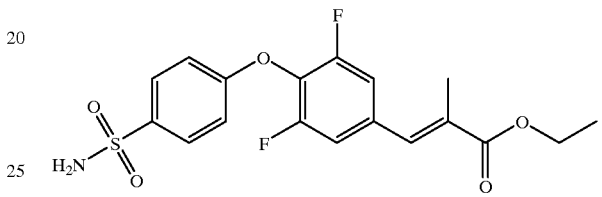

see Example 1.

Intermediate 3:

4-[2,6-Difluoro-4-(3-ethoxycarbonyl-3-methylpropen-1-yl)phenoxy]benzenesulfone-N-(carboxy-N'-methylamid)amide

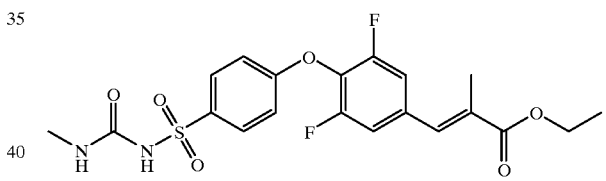

1.0 eq. of intermediate 2 is introduced into acetone and stirred under reflux for 1.5 h with 2.5 eq. of K$_2$CO$_3$. A solution of 2.5 eq. of methyl isocyanate in acetone is added dropwise and the mixture is heated further under reflux. After an increase in conversion is no longer detectable by means of LCMS, insoluble constituents are filtered off and the filtrate is concentrated in vacuo. The residue is taken up in H$_2$O and adjusted to pH 1 using 2 N HCl, the title compound precipitating. Filtering off with suction and drying in vacuo yields the desired sulfonylurea in good yield. (MS-ES+: 455.1).

4-[2,6-Difluoro-4-(3-guanidino-2-methyl-3-oxopropenyl)phenoxy]benzenesulfone-N-(carboxy-N'-methylamid)amide; HCl salt Intermediate 3 is reacted according to the variant described in 1 A and gives the corresponding cinnamic acid guanidide as a colorless solid. (MS-ES+: 468.; LCMS R$_t$=3.991 min).

Example 9

4-[2,6-Difluoro-4-(3-guanidino-2-methyl-3-oxopropenyl)phenoxy]benzenesulfone N-(carboxy-N'-ethylamid)amide; HCl salt

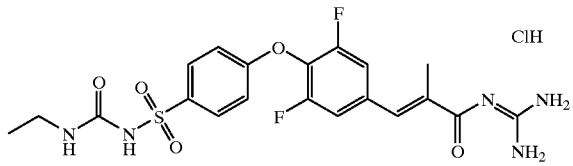

Intermediate 1:
Ethyl 2-methyl-3-(3,4,5-trifluorophenyl)acrylate

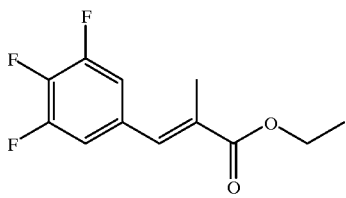

see Example 1.

Intermediate 2:
Ethyl 3-[3,5-difluoro-4-(4-sulfamoylphenoxy)phenyl]-2-methylacrylate

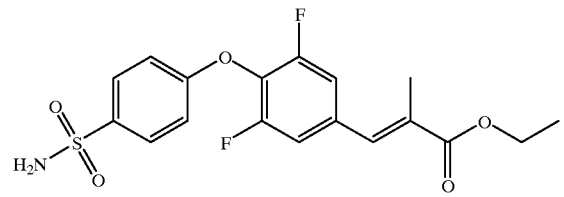

see Example 1.

Intermediate 3:
4-[2,6-Difluoro-4-(3-ethoxycarbonyl-3-methylpropen-1-yl)phenoxy]benzenesulfone N-(carboxy-N'-ethylamid)amide

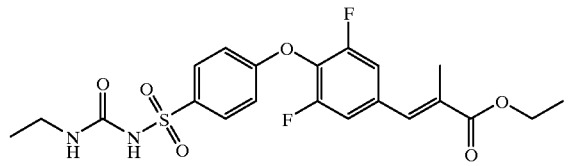

The analogous procedure as described in Example 8, intermediate 3, gives the title compound, starting from intermediate 2 and ethyl isocyanate, as a colorless solid. (MS-ES+: 469.1).

4-[2,6-Difluoro-4-(3-guanidino-2-methyl-3-oxopropenyl)phenoxy]benzenesulfone N-(carboxy-N'-ethylamid)amide; HCl salt Reaction of intermediate 3 according to the method described in 1 A gives the desired product as a colorless solid. (MS-ES+: 482.1; LCMS R$_t$=4.128 min).

Example 10

N-(2-Dimethylaminoethyl)-4-[4-(3-guanidino-2-methyl-3-oxopropenyl)phenylamino]-benzenesulfonamide; HCl salt

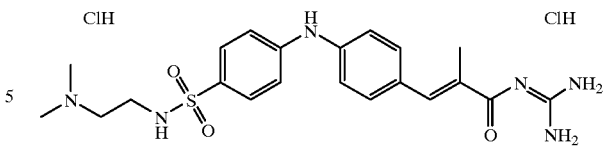

Intermediate 1:
Ethyl 2-methyl-3-(4-bromophenyl)acrylate

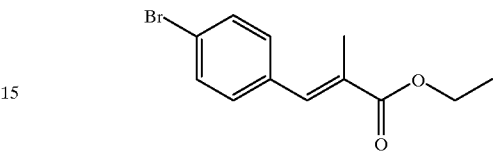

see Example 4.

Intermediate 2:
N-[4-(2-Dimethylaminoethylsulfamoyl)phenyl]acetamide

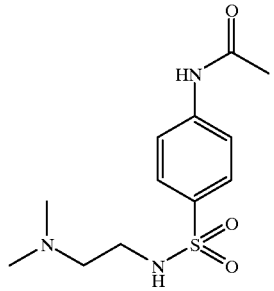

4-Acetylaminobenzenesulfonyl chloride is introduced into dichloromethane and treated at room temperature with two equivalents of N,N-dimethylethylenediamine and stirred at room temperature until complete conversion can be determined (LCMS). For work-up, the solvent is distilled off, the oily residue is taken up in dichloromethane or ethyl acetate and the mixture is washed with NaHCO$_3$ solution. The phases are separated and the aqueous phase is extracted once more with dichloromethane or ethyl acetate. The organic phases are dried using Na$_2$SO$_4$ and concentrated. The crude product thus obtained is reacted further without further purification. (MS-CI+: 286.0; LCMS R$_t$=2.542 min)

Intermediate 3:
4-Amino-N-(2-dimethylaminoethyl)benzenesulfonamide

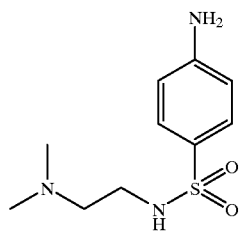

2.3 g of intermediate 2 are dissolved in 20 ml of methanol. After addition of 5.0 eq. of sodium methoxide, the mixture is heated under reflux until the reaction check indicates complete conversion. In order to accelerate the reaction, a further 10 to 15 eq. of sodium methoxide were added. After reaction is complete, the mixture is freed from the solvent and the residue is taken up in H$_2$O and adjusted to pH 8 using conc. HCl. The aqueous phase is extracted three times with ethyl acetate. The organic phases are dried using Na$_2$SO$_4$ and concentrated, the title compound being obtained in the form of a yellowish solid. (MS-ES+: 244.1; LCMS R$_t$=0.468 min)

Intermediate 4:

Ethyl 3-{4-[4-(2-dimethylaminoethylsulfamoyl) phenylamino]phenyl}-2-methylacrylate

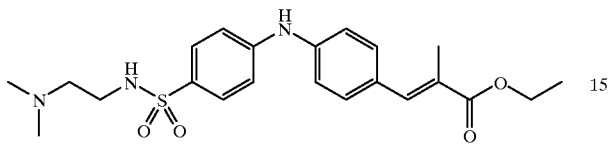

Starting from intermediate 1 and intermediate 3, the synthesis of the title compound proceeds analogously to the procedure for intermediate 3, Example 4, the solvent used being a mixture of toluene/DMF (1:1). After reaction is complete, the mixture is freed from the solvent and the residue is taken up in dichloromethane. The insoluble constituents are filtered off, the filtrate is concentrated and the residue is purified on silica gel. (MS-ES+: 432.3; LCMS R$_t$=4.407 min)

N-(2-Dimethylaminoethyl)-4-[4-(3-guanidino-2-methyl-3-oxopropenyl)phenylamino]-benzenesulfonamide; HCl salt Intermediate 4 is converted into the title compound according to method 1 A, the desired acylguanidide being obtained as a yellow solid. (MS-ES+: 445.3; 386.2; 193.6; LCMS R$_t$=3.552 min).

Example 11

4-[4-(3-Guanidino-2-methyl-3-oxopropenyl)phenylamino]-N-(2-pyrrolidin-1-ylethyl)-benzenesulfonamide; HCl salt

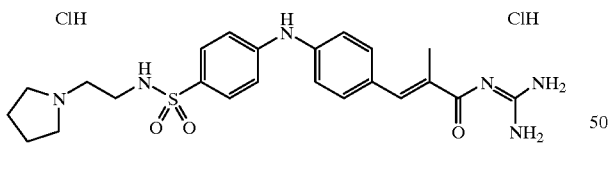

Intermediate 1:

Ethyl 2-methyl-3-(4-bromophenyl)acrylate

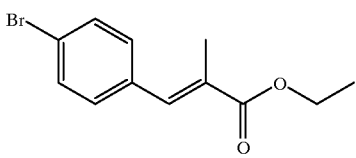

see Example 4.

Intermediate 2:
N-[4-(2-Pyrrolidin-1-ylethylsulfamoyl)phenyl]acetamide

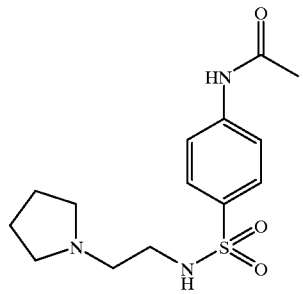

Starting from 4-acetylaminobenzenesulfonyl chloride and 2-pyrrolidin-1-ylethylamine, the title compound is prepared analogously to the method described in Example 10, intermediate 2. The crude product thus obtained can be used for further reaction without further purification. (MS-ES+: 312.1; LCMS R$_t$=1.957 min)

Intermediate 3:
4-Amino-N-(2-pyrrolidin-1-ylethyl)benzenesulfonamide

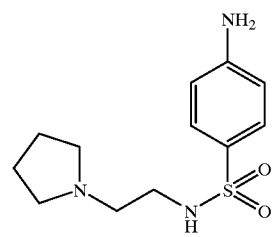

The acetal protective group is removed analogously to the method described in Example 10, intermediate 3. (MS-ES+: 270.2; LCMS R$_t$=0.511 min)

Intermediate 4:
Ethyl 2-methyl-3-{4-[4-(2-pyrrolidin-1-ylethylsulfamoyl) phenylamino]phenyl}acrylate

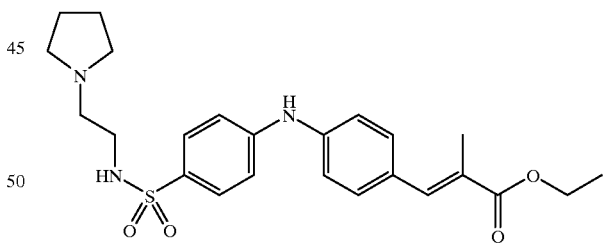

The coupling reaction is carried out according to the method described in Example 10, intermediate 4. (MS-ES+: 458.3; LCMS R$_t$=4.498 min)

4-[4-(3-Guanidino-2-methyl-3-oxopropenyl)phenylamino]-N-(2-pyrrolidin-1-ylethyl)benzenesulfonamide; HCl salt Reaction of the ethyl ester described as intermediate 4 according to the general method described in variant 1 A gives the desired cinnamic acid guanidide as a yellow solid. (MS-ES+: 471.4; 412.3; 206.7; LCMS R$_t$=3.634 min)

Example 12

N-(2-Methyl-3-{4-[4-(4-methylpiperazine-1-sulfonyl) phenylamino]phenyl}acryloyl)-guanidine; HCl salt

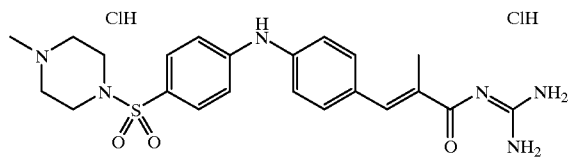

Intermediate 1:

Ethyl 2-methyl-3-(4-bromophenyl)acrylate

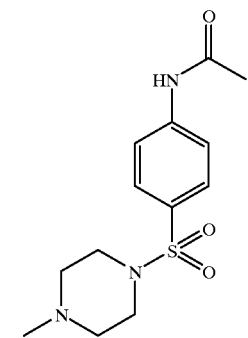

see Example 4.

Intermediate 2:

N-[4-(4-Methylpiperazine-1-sulfonyl)phenyl]acetamide

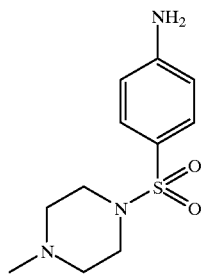

The analogous procedure to that in Example 10, intermediate 2, gives the title compound in the form of a yellowish solid in a yield of 84%. (MS-ES+: 298.1; LCMS $R_t$=1.964 min)

Intermediate 3:

4-(4-Methylpiperazine-1-sulfonyl)phenylamine

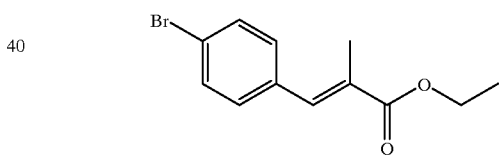

Starting from intermediate 2, the desired aniline is prepared according to the method indicated in Example 10, intermediate 3. (MS-ES+: 256.1; LCMS $R_t$=1.275 min)

Intermediate 4:

Ethyl 2-methyl-3-{4-[4-(4-methylpiperazine-1-sulfonyl)phenylamino]phenyl}acrylate

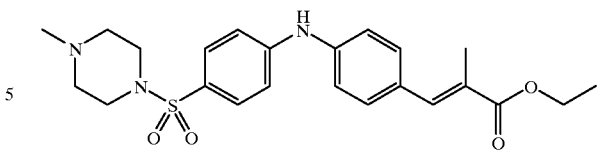

The synthesis is carried out by reaction of intermediate 3 with intermediate 1 according to the method described in Example 1 0, intermediate 4, in pure toluene as solvent. For work-up, the mixture is freed from the solvent and the residue is taken up in dichloromethane. Insoluble constituents are filtered off and the filtrate is purified on silica gel, the title compound being obtained in almost quantitative yield. (MS-ES+: 444.3; LCMS $R_t$=4.539 min)

N-(2-Methyl-3-{4-[4-(4-methylpiperazine-1-sulfonyl)phenylamino]phenyl}acryloyl)-guanidine; HCl salt The ethyl ester described in intermediate 4 is reacted with guanidine according to general variant 1 A and gives the desired guanidide in the form of a yellow solid. (MS-ES+: 457.3; 398.2; 220.1; LCMS $R_t$=3.651 min)

Example 13

4-[4-(3-Guanidino-2-methyl-3-oxopropenyl)phenylamino]-N-methyl-N-(1-methyl-pyrrolidin-3-yl)benzenesulfonamide, HCl salt

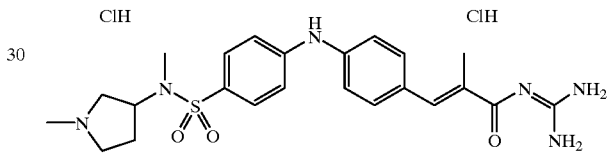

Intermediate 1:

Ethyl 2-methyl-3-(4-bromophenyl)acrylate

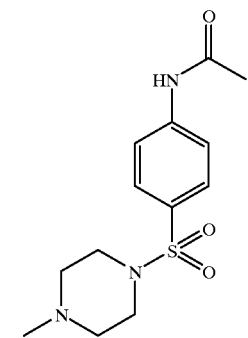

see Example 4.

Intermediate 2:

N-{4-[Methyl-(1-methylpyrrolidin-3-yl)sulfamoyl]phenyl}acetamide

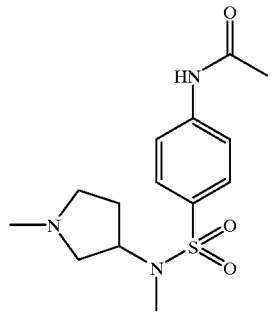

4-Acetylaminobenzenesulfonyl chloride and methyl-(1-methylpyrrolidin-3-yl)amine are reacted according to the method described in Example 10, intermediate 2. The title compound obtained in the form of a slightly yellowish solid can be reacted further without further purification. (MS-ES+: 312.1; LCMS $R_t$=0.698 min)

Intermediate 3:

4-Amino-N-methyl-N-(1-methylpyrrolidin-3-yl) benzenesulfonamide

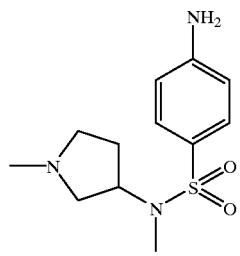

Starting from intermediate 2, the desired aniline is prepared according to the method indicated in Example 10, intermediate 3. (MS-CI+: 270.2; LCMS $R_t$=1.922 min)

Intermediate 4

Ethyl 2-methyl-3-(4-{4-[methyl-(1-methylpyrrolidin-3-yl)sulfamoyl]phenylamino}-phenyl)acrylate

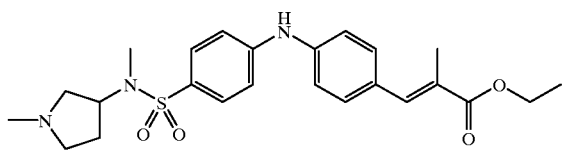

The title compound is synthesized by palladium-catalyzed reaction of intermediate 3 with intermediate 1 according to the method described in Example 10, intermediate 4. After purification on silica gel, the desired product can be isolated in 71% yield. (MS-ES+: 458.4; LCMS $R_t$=4.547 min)

4-[4-(3-Guanidino-2-methyl-3-oxopropenyl)phenylamino]-N-methyl-N-(1-methyl-pyrrolidin-3-yl) benzenesulfonamide, HCl salt Intermediate 4 is converted into the corresponding cinnamic acid guanidide according to general variant 1 A, the isolated yield being 78%. (MS-ES+: 471.4; 412.3; 206.7; LCMS $R_t$=3.685 min)

Example 14

4-[4-(3-Guanidino-2-methyl-3-oxopropenyl)phenylamino]-N-methylbenzenesulfonamide; HCl salt

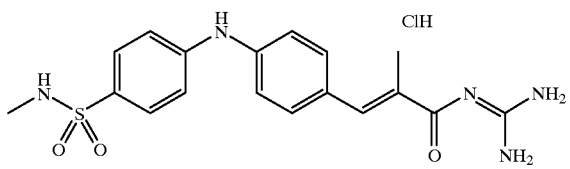

Intermediate 1:
Ethyl 2-methyl-3-(4-bromophenyl)acrylate

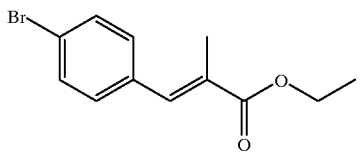

see Example 4.
Intermediate 2:
N-(4-Methylsulfamoylphenyl)acetamide

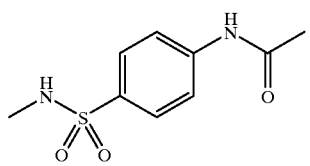

10.5 g (45 mmol) of 4-acetylaminobenzenesulfonyl chloride are stirred at 50° C. for 3 hours in 100 ml of 40% strength methylamine solution. The solution is then extracted three times with ethyl acetate. The organic phases are dried using $Na_2SO_4$ and concentrated. The residue is stirred with dichloromethane and the insoluble constituents are filtered off. Concentration of the filtrate gives the desired sulfonamide in adequate purity and almost quantitative yield. (MS-CI+: 229.1; LCMS $R_t$=3.249 min)
Intermediate 3:
4-Amino-N-methylbenzenesulfonamide

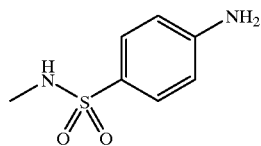

Starting from intermediate 2, the acetyl group is removed according to the method described in Example 10, intermediate 3. (MS-CI+: 187.1; LCMS $R_t$=1.358 min)
Intermediate 4:
Ethyl 2-methyl-3-[4-(4-methylsulfamoylphenylamino)phenyl]acrylate

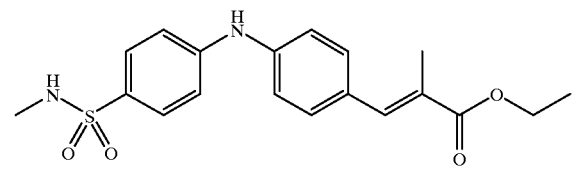

Intermediate 1 is reacted with intermediate 3 in the manner described in Example 10, intermediate 4, the desired ethyl ester being obtained in the form of a yellowish oil. (MS-CI+: 375.1; LCMS $R_t$=5.064 min)
4-[4-(3-Guanidino-2-methyl-3-oxopropenyl)phenylamino]-N-methylbenzenesulfonamide; HCl salt
Intermediate 4 is reacted with guanidine according to the general method described in variant 1 A, the title compound being obtained in the form of a yellow solid. The yield is 88%. (MS-ES+: 388.1; 329.1; LCMS $R_t$=4.126 min).

Pharmacological Data

Test Description

In this test, the recovery of the intracellular pH ($pH_i$) which commences with functional NHE after acidification even under bicarbonate-free conditions. For this, the $pH_i$ was determined using the pH-sensitive fluorescent dye BCECF (Calbiochem, the precursor BCECF-AM is employed). The cells were first loaded with BCECF. The BCECF fluorescence was determined in a ratio fluorescence spectrometer (Photon Technology International, South Brunswick, N.J., USA) at excitation wavelengths of 505 and 440 nm and an emission wavelength of 535 nm and converted into the $pH_i$ by means of calibration curves. During BCECF loading, the cells were already incubated in $NH_4Cl$ buffer (pH 7.4) ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml of BSA; a pH of 7.4 is set using 1 M NaOH). The intracellular acidification was induced by addition of 975 µl of an $NH_4Cl$-free buffer (see below) to 25 µl aliquots of the cells incubated in $NH_4Cl$ buffer. The subsequent rate of the pH recovery was recorded for 2 minutes in the case of NHE1, for 5 minutes in the case of NHE2 and 3 minutes in the case of NHE3. For the calculation of the inhibitory potency of the tested substances, the cells were first investigated in buffers in which a complete recovery or no pH recovery at all took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 is set using 1 M NaOH). For the determination of the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 is set using 1 M NaOH). The substances to be tested were applied in the $Na^+$-containing buffer. The recovery of the intracellular pH at any tested concentration of a substance was expressed as a percentage of the maximum recovery. By means of the program Sigma Plot, the $IC_{50}$ value of the respective substance for the individual NHE subtypes was calculated from the percentage values of the pH recovery.

Example 1: $IC_{50}(rNHE3)=0.07$ µM
Example 2: $IC_{50}(rNHE3)=0.02$ µM
Example 3: $IC_{50}(rNHE3)=0.13$ µM
Example 4: $IC_{50}(rNHE3)=0.62$ µM
Example 5: $IC_{50}(rNHE3)=1.20$ µM
Example 6: $IC_{50}(rNHE3)=0.06$ µM
Example 7: $IC_{50}(rNHE3)=2.60$ µM
Example 8: $IC_{50}(rNHE3)=0.09$ µM
Example 9: $IC_{50}(rNHE3)=0.07$ µM
Example 10: $IC_{50}(rNHE3)=1.10$ µM
Example 11: $IC_{50}(rNHE3)=0.85$ µM
Example 12: $IC_{50}(rNHE3)=2.60$ µM
Example 13: $IC_{50}(rNHE3)=0.59$ µM
Example 14: $IC_{50}(rNHE3)=0.85$ µM Solubilities The solubilities indicated below are determined by UV spectroscopy in a 0.9% strength NaCl solution.

Example 6: 1.86 mg/ml
Example 7: >2.19 mg/ml
Example 10: 1.28 mg/ml
Example 11: 1.52 mg/ml
Example 12: 1.76 mg/ml
Example 13: 3.08 mg/ml

We claim:
1. A compound of the formula I,

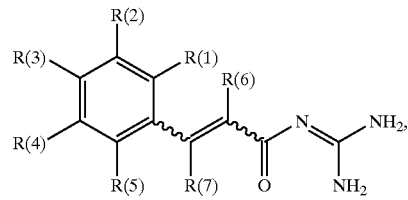

in which:
at least one of R(1), R(2), R(3), R(4) and R(5) is —$X_a$—$Y_b$—$L_n$—U;
X is CR(16)R(17), O, S or NR(18);
  where R(16), R(7) and R(18) independently of one another are H or an alkyl having 1, 2, 3 or 4 carbon atoms, where the alkyl is chosen from unsubstituted alkyls, partially fluorinated alkyls and completely fluorinated alkyls;
a is zero or 1;
Y is alkylene having 1, 2, 3, 4, 5, 6, 7 or 8 carbon atoms, alkylene-T having 1, 2, 3, 4, 5, 6, 7 or 8 carbon atoms in the alkylene group, T, or T-alkylene having 1, 2, 3, 4, 5, 6, 7 or 8 carbon atoms in the alkylene group;
  where T is NR(20), phenylene, O or S, where the phenylene is not substituted or is substituted by 1–3 substituents chosen from F, Cl, $CF_3$, methyl, methoxy and NR(21)R(22);
    where R(20), R(21) and R(22) independently of one another are H or an alkyl having 1, 2, 3 or 4 carbon atoms, where the alkyl is chosen from unsubstituted alkyls, partially fluorinated alkyls and completely fluorinated alkyls;
b is zero or 1;
L is O, S, NR(23) or $C_kH_{2k}$;
  where k is 1, 2, 3, 4, 5, 6, 7 or 8;
  where R(23) is H or an alkyl group having 1, 2, 3 or 4 carbon atoms, where the alkyl is chosen from unsubstituted alkyls, partially fluorinated alkyls and completely fluorinated alkyls;
n is zero or 1;
U is

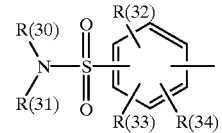

or a nitrogen-containing heterocycle having 1, 2, 3, 4, 5, 6, 7, 8 or 9 carbon atoms, which is substituted by an —$SO_2NR(30)R(31)$-group;
  where R(30) and R(31) independently of one another are H or an alkyl group having 1, 2, 3, 4, 5, 6, 7 or 8 carbon atoms,
    where in the alkyl group, independently of one another, one or more $CH_2$ groups can be replaced by O, NR(35), C=O, S or C=S;
    where R(35) is H or alkyl having 1, 2, 3 or 4 carbon atoms, where the alkyl is chosen from unsubstituted alkyls, partially fluorinated alkyls and completely fluorinated alkyls; or
  R(30) and R(31) independently of one another are H, an alkyl having 1, 2, 3, 4, 5, 6, 7 or 8 carbon atoms, where the alkyl is chosen from partially fluorinated alkyls and completely fluorinated alkyls, $(C_3-C_8)$-cycloalkyl, phenyl-$(C_1-C_4)$-alkyl or $(C_3-C_8)$-cycloalkyl-$(C_1-C_4)$-alkyl,
    where in the alkyl or in the cycloalkyl ring, independently of one another, one or more $CH_2$ groups can be replaced by O, NR(35), C=O, S or C=S; or
R(30) and R(31) together are 4 or 5 methylene groups,
    where, independently of one another, one or more $CH_2$ groups can be replaced by O, NR(35), C=O, S or C=S; or
R(31) and R(35) together are 4 or 5 methylene groups;
R(32), R(33) and R(34) independently of one another are H, F, Cl, Br, I, $(C_1-C_4)$-alkyl, partially fluorinated $(C_1-C_4)$-alkyl, completely fluorinated $(C_1-C_4)$-alkyl, O—$(C_1-C_4)$-alkyl, partially fluorinated O—$(C_1-C_4)$-alkyl, completely fluorinated O—$(C_1-C_4)$-alkyl, $NO_2$, or NR(28)R(29);
    where R(28) and R(29) independently of one another are H or an alkyl having 1, 2, 3 or 4 carbon atoms, where the alkyl is chosen from unsubstituted alkyls, partially fluorinated alkyls and completely fluorinated alkyls;
where the N-containing heterocycles are N- or C-bridged and are unsubstituted or are substituted by 1–3 substituents selected from the group consisting of F, Cl, $CF_3$, methyl, methoxy and NR(36)R(37);
R(36) and R(37) independently of one another are H, an alkyl having 1, 2, 3 or 4 carbon atoms, where the alkyl is chosen from unsubstituted alkyls, partially fluorinateds, and completely fluorinated alkyls, or benzyl;
and the remaining substituents of R(1), R(2), R(3), R(4) and R(5) independently of one another are H, F, Cl, Br, I, $SO_2NH_2$, $SO_2CH_3$, $NO_2$, NR(24)R(25), CN, unsubstituted $(C_1-C_8)$-alkyl, partially fluorinated $(C_1-C_8)$-alkyl, completely fluorinated $(C_1-C_8)$-alkyl, unsubstituted O—$(C_1-C_8)$-alkyl, partially fluorinated O—$(C_1-C_8)$-alkyl, completely fluorinated O—$(C_1-C_8)$-alkyl, $(C_3-C_8)$-cycloalkyl, $(C_3-C_8)$-cycloalkyl-$(C_1-C_4)$-alkyl or phenyl-$(C_1-C_4)$-alkyl,
    where the phenyl is not substituted or is substituted by 1–3 substituents selected from the group consisting of F, Cl, $CF_3$, methyl, methoxy and NR(11)R(12);
R(11), R(12), R(24) and R(25) independently of one another are H or an alkyl having 1, 2, 3 or 4 carbon atoms, where the alkyl is chosen from unsubstituted alkyls, partially fluorinated alkyls and completely fluorinated alkyls;
R(6) and R(7) independently of one another are H, F, Cl, Br, I, CN, an alkyl having 1, 2, 3, 4, 5, 6, 7 or 8 carbon atoms, where the alkyl is chosen from unsubstituted alkyls, partially fluorinated alkyls, and completely fluorinated alkyls, cycloalkyl having 3, 4, 5, 6, 7 or 8 carbon atoms or phenyl,
    where the phenyl is not substituted or is substituted by 1–3 substituents selected from the group consisting of F, Cl, $CF_3$, methyl, methoxy and NR(14)R(15);
R(14) and R(15) independently of one another are H or an alkyl having 1, 2, 3 or 4 carbon atoms, where the alkyl is chosen from unsubstituted alkyls, partially fluorinated alkyls and completely fluorinated alkyls;
or a pharmaceutically tolerable salt thereof, in any stereoisomeric form, or a mixture of any such compounds in any ratio.

2. The compound of the formula I as claimed in claim 1, in which:
at least one of the substituents R(1), R(2), R(3), R(4) and R(5) is —X—U;
X is CR(16)R(17), O, S or NR(18);
R(16), R(17) and R(18) independently of one another are H or an alkyl having 1, 2, 3 or 4 carbon atoms, where the alkyl is chosen from unsubstituted alkyls, partially fluorinated alkyls and completely fluorinated alkyls;
U is or a nitrogen-containing heterocycle having 1, 2, 3, 4, 5, 6, 7, 8 or 9 carbon atoms, which is substituted by an —$SO_2$NR(30)R(31)-group;
R(30) and R(31) independently of one another are hydrogen or alkyl having 1, 2, 3, 4, 5, 6, 7 or 8 carbon atoms,
    where in the alkyl chain, independently of one another, one or more $CH_2$ groups can be replaced by O, NR(35), C=O, S or C=S;
R(35) is H or an alkyl having 1, 2, 3, 4 or 5 carbon atoms, where the alkyl is chosen from unsubstituted alkyls, partially fluorinated alkyls and completely fluorinated alkyls; or
R(30) and R(31) independently of one another are H, an alkyl having 1, 2, 3, 4, 5, 6, 7 or 8 carbon atoms, where the alkyl is chosen from partially fluorinated alkyl and completely fluorinated alkyl, $(C_3-C_8)$-cycloalkyl, phenyl-$(C_1-C_4)$-alkyl or $(C_3-C_8)$-cycloalkyl-$(C_1-C_4)$-alkyl,
    where in the alkyl or in the cycloalkyl ring, independently of one another, one or more $CH_2$ groups can be replaced by O, NR(35), C=O, S or C=S; or
R(30) and R(31) together are 4 or 5 methylene groups,
    where, independently of one another, one or more CH2 groups can be replaced by O, NR(35), C=O, S or C=S; or
R(31) and R(35) together are 4 or 5 methylene groups;
R(32), R(33) and R(34) independently of one another are H, F, Cl, Br, I, $(C_1-C_4)$-alkyl, O—$(C_1-C_4)$-alkyl, $CF_3$ or NR(28)R(29);
    R(28) and R(29) independently of one another are H or alkyl having 1, 2, 3 or 4 carbon atoms;
where the N-containing heterocycles are N- or C-bridged and are not substituted or are substituted by 1–3 substituents selected from the group consisting of F, Cl, $CF_3$, methyl, methoxy and NR(36)R(37);
R(36) and R(37) independently of one another are H, an alkyl having 1, 2, 3 or 4 carbon atoms, where the alkyl is chosen from unsubstituted alkyls, partially fluorinateds, and completely fluorinated alkyls, or benzyl;
and the remaining substituents of R(1), R(2), R(3), R(4) and R(5) independently of one another are H, F, Cl, Br, I, $SO_2NH_2$, $SO_2CH_3$, $NO_2$, NR(24)R(25), CN, unsubstituted (C₁–C₄)-alkyl, partially fluorinated (C₁–C₄)-alkyl, completely fluorinated (C₁–C₄)-alkyl, unsubstituted O—(C₁–C₄)-alkyl, partially fluorinated O—(C₁–C₄)-alkyl, completely fluorinated O—(C₁–C₄)-alkyl, (C₃–C₆)-cycloalkyl, (C₃–C₆)-cycloalkyl-(C₁–C₄)-alkyl or phenyl-(C₁–C₄)-alkyl, where the phenyl is not substituted or is substituted by 1–3 substituents selected from the group consisting of F, Cl, CF₃, methyl, methoxy and NR(11)R(12);

R(11), R(12), R(24) and R(25) independently of one another are H or an alkyl having 1, 2, 3 or 4 carbon atoms, where the alkyl is chosen from unsubstituted alkyls, partially fluorinated alkyls, and completely fluorinated alkyls;

R(6) and R(7) independently of one another are hydrogen, F, Cl, Br, I, CN, an alkyl having 1, 2, 3, 4, 5, 6, 7 or 8 carbon atoms, where the alkyl is chosen from unsubstituted alkyls, partially fluorinated alkyls, and completely fluorinated alkyls, cycloalkyl having 3, 4, 5, 6, 7 or 8 carbon atoms or phenyl, which is not substituted or is substituted by 1–3 substituents selected from the group consisting of F, Cl, CF₃, methyl, methoxy and NR(14)R(15);

R(14) and R(15) independently of one another are H, alkyl having 1, 2, 3 or 4 carbon atoms, where the alkyls are chosen from unsubstituted alkyls, partially fluorinated alkyls and completely fluorinated alkyls;

or a pharmaceutically tolerable salt thereof, in any stereoisomeric form, or a mixture of any such compounds in any ratio.

3. The compound of the formula I as claimed in claim 1, in which:

at least one of the substituents R(1), R(2), R(3), R(4) and R(5) is —X—U;

X is CR(16)R(17), O, S or NR(18);

R(16), R(17) and R(18) independently of one another are H, alkyl having 1, 2, 3 or 4 carbon atoms or CF₃;

U is

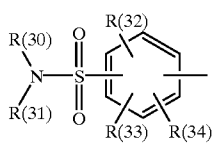

or a nitrogen-containing heterocycle having 1, 2, 3, 4, 5 or 6 carbon atoms, which is substituted by an —SO₂NR(30)R(31) group;

R(30) and R(31) independently of one another are H, alkyl having 1, 2, 3, 4, 5, 6, 7 or 8 carbon atoms, CF₃, (C₃–C₈)-cycloalkyl, where in the alkyl, independently of one another, one or more CH₂ groups can be replaced by O, NR(35), C═O, S or C═S;

where R(35) is H or alkyl having 1, 2, 3, 4 or 5 carbon atoms; or

R(30) and R(31) together are 4 or 5 methylene groups, where, independently of one another, one or more CH₂ groups can be replaced by O, NR(35), C═O, S or C═S; or R(31) and R(35) together are 4 or 5 methylene groups;

R(32), R(33) and R(34) independently of one another are H, F, Cl, methyl, ethyl, Omethyl, Oethyl, CF₃, NH₂, NHmethyl or Nmethyl₂;

where the N-containing heterocycles are N- or C-bridged and are not substituted or are substituted by 1–3 substituents selected from the group consisting of F, Cl, CF₃, methyl, methoxy and NR(36)R(37);

R(36) and R(37) independently of one another are H, alkyl having 1, 2, 3 or 4 carbon atoms, CF₃ or benzyl;

and the remaining substituents of R(1), R(2), R(3), R(4) and R(5) independently of one another are H, F, Cl, Br, I, SO₂NH₂, SO₂CH₃, NR(24)R(25), CN, (C₁–C₄)-alkyl, CF₃, C₂F₅, O—(C₁–C₄)-alkyl, OCF₃, OC₂F₅, (C₃–C₆)-cycloalkyl, (C₃–C₈)-cycloalkyl-(C₁–C₄)-alkyl or phenyl-(C₁–C₄)-alkyl, where the phenyl is not substituted or is substituted by 1–3 substituents selected from the group consisting of F, Cl, CF₃, methyl, methoxy and NR(11)R(12);

R(11), R(12), R(24) and R(25) independently of one another are H or alkyl having 1, 2, 3 or 4 carbon atoms;

R(6) and R(7) independently of one another are hydrogen, F, Cl, Br, I, CN, alkyl having 1, 2, 3, 4, 5, 6, 7 or 8 carbon atoms, CF₃, cycloalkyl having 3, 4, 5 or 6 carbon atoms;

or a pharmaceutically tolerable salt thereof, in any stereoisomeric form, or a mixture of any such compounds in any ratio.

4. The compound of the formula I as claimed in claim 1, in which:

at least one of the substituents R(1), R(2), R(3), R(4) and R(5) is —X—U;

X is CR(16)R(17), O, S or NR(18);

R(16), R(17) and R(18) independently of one another are H, CH₃, C₂H₅ or CF₃;

U is

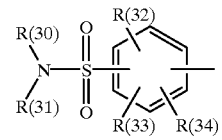

or an N-containing heterocycle having 3, 4 or 5 carbon atoms, which is substituted by an —SO₂NR(30)R(31)-group;

R(30) and R(31) independently of one another are hydrogen or alkyl having 1, 2, 3, 4, 5, 6, 7 or 8 carbon atoms, CF₃, (C₃–C₈)-cycloalkyl;

where in the alkyl, independently of one another, one or more CH₂ groups can be replaced by O, NR(35), C═O, S or C═S;

R(35) is H or alkyl having 1, 2, 3, 4 or 5 carbon atoms; or

R(30) and R(31) together are 4 or 5 methylene groups, where, independently of one another, one or more CH₂ groups can be replaced by O, NR(35), C═O, S or C═S; or R(31) and R(35) together are 4 or 5 methylene groups;

R(32), R(33) and R(34) independently of one another are H, F, Cl, methyl, CF₃;

where the N-containing heterocycles are N- or C-bridged and are not substituted or are substituted by 1–3 substituents selected from the group consisting of F, Cl, CF₃, methyl, methoxy and NR(36)R(37);

R(36) and R(37) independently of one another are H, CH$_3$, C$_2$H$_5$ or CF$_3$;

and the remaining substituents of R(1), R(2), R(3), R(4) and R(5) independently of one another are H, F, Cl, SO$_2$NH$_2$, SO$_2$CH$_3$, NR(24)R(25), CN, (C$_1$–C$_4$)-alkyl, CF$_3$, C$_2$F$_5$, O—(C$_1$–C$_4$)-alkyl, OCF$_3$, OC$_2$F$_5$, (C$_3$–C$_6$)-cycloalkyl or (C$_3$–C$_6$)-cycloalkyl-(C$_1$–C$_4$)-alkyl;

R(24) and R(25) independently of one another are H, alkyl having 1, 2, 3 or 4 carbon atoms;

R(6) and R(7) independently of one another are H, F, Cl, Br, I, CN, CH$_3$, C$_2$H$_5$, CF$_3$ or cycloalkyl having 3, 4, 5 or 6 carbon atoms;

or a pharmaceutically tolerable salt thereof, in any stereoisomeric form, or a mixture of any such compounds in any ratio.

5. A process for the preparation of a compound I as claimed in claim 1 comprising reacting a compound of formula II

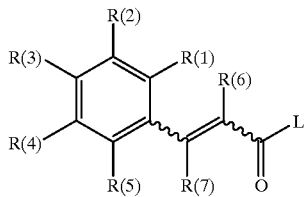

in which R(1) to R(7) are as defined in claim 1, and L is an easily substitutable leaving group, with guanidine.

6. A method of treating arrhythmias comprising administering to a patient in need thereof an effective amount of at least one compound chosen from the compounds as claimed in claim 1.

7. A method of treating or preventing cardiac infarct comprising administering to a patient in need thereof an effective amount of at least one compound chosen from the compounds as claimed in claim 1.

8. A method of treating or preventing angina pectoris comprising administering to a patient in need thereof an effective amount of at least one compound chosen from the compounds as claimed in claim 1.

9. A method of treating or preventing ischemic conditions of the heart comprising administering to a patient in need thereof an effective amount of at least one compound chosen from the compounds as claimed in claim 1.

10. A method of treating or preventing ischemic conditions of the peripheral or central nervous system or stroke of the heart comprising administering to a patient in need thereof an effective amount of at least one compound chosen from the compounds as claimed in claim 1.

11. A method of treating or preventing ischemic conditions of peripheral organs and limbs comprising administering to a patient in need thereof an effective amount of at least one compound chosen from the compounds as claimed in claim 1.

12. A method of treating a state of shock comprising administering to a patient in need thereof an effective amount of at least one compound chosen from the compounds as claimed in claim 1.

13. A method of preserving and storing a transplant for surgical measure, comprising contacting the transplant with an effective amount of at least one compound chosen from the compounds as claimed in claim 1.

14. A method of treating cell proliferation comprising administering to a patient in need thereof an effective amount of at least one compound chosen from the compounds as claimed in claim 1.

15. A pharmaceutical comprising an efficacious amount of at least one compound chosen from the compounds as claimed in claim 1.

* * * * *

UNITED STATES PATENT AND TRADEMARK OFFICE
CERTIFICATE OF CORRECTION

PATENT NO. : 6,399,824 B1
DATED : June 4, 2002
INVENTOR(S) : Hofmeister et al.

It is certified that error appears in the above-identified patent and that said Letters Patent is hereby corrected as shown below:

<u>Title page, Item [54] and Column 1, line 1,</u>
Title, after "CINNAMIC", delete the comma.

<u>Column 30,</u>
Line 18, "R(7)" should read -- R(17) --.
Line 22, "or1" should read -- or 1 --.

<u>Column 32,</u>
Line 46, "CH2" should read -- $CH_2$ --.

<u>Column 33,</u>
Line 2, "$(C_1-C_4)$-alkyl" should read -- $(C_1-C_4)$-alkyl --.
Line 23, "NR(1 4)R(15)" should read -- NR(14)R(15) --.

<u>Column 34,</u>
Line 13, "$(C_3-C_8)$" should read -- $(C_3-C_6)$ --.

Signed and Sealed this

Twenty-eighth Day of January, 2003

JAMES E. ROGAN
*Director of the United States Patent and Trademark Office*